United States Patent [19]
Phillips et al.

[11] Patent Number: 4,755,624
[45] Date of Patent: Jul. 5, 1988

[54] LOW PRESSURE HYDROFORMYLATION PROCESS

[75] Inventors: Gerald W. Phillips; Thomas J. Devon; Thomas A. Puckette; Jerome L. Stavinoha; Jeffrey J. Vanderbilt, all of Longview, Tex.

[73] Assignee: Eastman Kodak Company, Rochester, N.Y.

[21] Appl. No.: 16,155

[22] Filed: Feb. 18, 1987

[51] Int. Cl.$^4$ .............................................. C07C 45/50
[52] U.S. Cl. .................................. 568/454; 502/162; 502/166
[58] Field of Search ............... 568/454, 451; 502/162, 502/166

[56] References Cited

U.S. PATENT DOCUMENTS 4,694,109 9/1987 Devon et al. ...................... 568/454

OTHER PUBLICATIONS

Maigrot et al., "Synthesis", p. 317, (1985).
Bestmann et al., "Chem. Ber.", vol. 107, (1974).
Tamao et al., "Tetrahedron Letter, No. 16, pp. 1389-1392, (1977).

Primary Examiner—Werren B. Lone
Attorney, Agent, or Firm—S. E. Reiter; William P. Heath, Jr.; John F. Stevens

[57] ABSTRACT

A hydroformylation process comprising contacting hydroformylation stock in a reaction zone at a temperature of from about 20° C. to about 250° C. and a pressure of from about 15 psig to about 800 psig with hydrogen, carbon monoxide and a catalyst comprising rhodium in chemical complex with one or more ligands of the formula

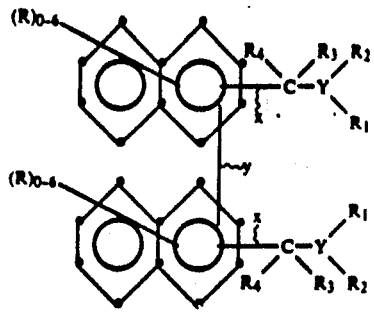

wherein:
the x and y bonds are adjacent on ring structures,
each R when present as a substituent is independently selected from hydrogen, alkyl, alkoxy, aryloxy, aryl, cyano, aralkyl, alkaryl, or the like;
each $R_1$ and $R_2$ is independently selected from alkyl, aryl, aralkyl, or the like;
each $R_3$ and $R_4$ is independently selected from hydrogen and the $R_1$ substituents; and
each Y is independently selected from the elements N, P, As, Sb and Bi.

10 Claims, No Drawings

LOW PRESSURE HYDROFORMYLATION PROCESS

This invention concerns a low pressure hydroformylation process wherein one or more olefins and/or nonconjugated diolefins, and/or other unsaturated organic compounds, all hereinafter referred to as hydroformylation stock, may be converted to aldehydes for use as such or for conversion by known methods, to products such as alcohols and acids. More particularly the invention concerns oxo or hydroformylation processes designed for relatively low pressure operation for the preparation of unusually high proportions of normal or unbranched aldehydes from α-olefins, particularly n-butyraldehyde from propylene.

The present ligands are compounds of the general formula

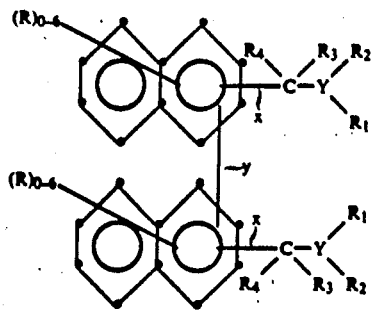

wherein:
  the x bounds are adjacent the y bonds on the ring structures;
  each R when present as a substituent is independently selected from alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;
  each $R_1$ and $R_2$ is independently selected from alkyl, aryl, aralkyl, alkaryl or cycloaliphatic;
  each $R_3$ and $R_4$ is independently selected from hydrogen and the $R_1$ substituents;
  each of the above alkyl groups or moieties is straight or branched chain of 1–20 carbons, preferably 1–8 carbons, each aryl group contains 6–10 ring carbons, and each cycloaliphatic group contains from 4–6 ring carbons; and
  each Y is independently selected from the elements N, P, As, Sb and Bi, with P being preferred.

The present hydroformylation process in its broad sense comprises contacting at least one olefin having from 2 to 20 carbon atoms in a reaction zone at a temperature of from about 20° C. to about 250° C. and a pressure of from about 15 psig to about 800 psig with syn gas ($H_2$, CO) and a catalyst comprising rhodium in chemical complex with one or more of the above ligands for a sufficient period of time to permit reaction of said olefin with said syn gas to form aldehyde product.

The present ligands, in particular, the 2,2'-bis(diphenylphosphinomethyl)-1,1'-binaphthyl (hereinafter, NAPHOS) have special utility as a bidentate ligand modifier for the low pressure rhodium hydroformylation of alpha-olefins to prepare aldehyde products with unusually high ratios of normal to branched isomers. This invention effects the efficient use of olefinic feedstocks to prepare desirable linear aldehyde products in high yield. Such products from propylene include n-butyraldehyde which is used to prepare the commercial solvent n-butanol. The hydroformylation of 1-butene and 1-pentene yield intermediate aldehyde products useful for the preparation of the solvents 1-pentanol and 1-hexanol, respectively. The hydroformylations of 1-hexene and 1-octene yield aldehyde products used to prepare the commercially valuable carboxylic acids, n-heptanoic acid and n-nonanoic acid. These same aldehyde products may be converted into alcohols useful for the preparation of plasticizers, synthetic lubricants, and detergents. Likewise, the hydroformylation of higher olefins such as 1-decene and 1-dodecene yield aldehyde precursors to 1-undecanol and 1-hydroxytridecane useful as fabric softeners and ingredients in plasticizers and detergents. These ligands show improvements in hydroformylation technology in one or more areas such as high normal to iso ratios employing relatively small amounts of ligand, effective in low pressure systems, increased catalytic activity and retention thereof over extended periods, and increased catalyst stability. The ligands of the invention are particularly useful in their unique ability to produce the desired high normal/iso ratios even at desirable low levels of ligand. Alpha-olefins with heteroatom substitution on the molecule such as allyl alcohol, allyl acetate, 4-hydroxybutene-1, and the like may also be used in this invention. Also, branched olefins such as isobutene and internal olefins such as cis-butene-2 may be used herein as feedstocks for the preparation of aldehyde products. Diolefins such as 1,7-octadiene and the like may also be used to prepare dialdehyde products provided that the two carbon-carbon double bonds are not in conjugation.

As a general statement of the actual chemical composition of the present active catalyst species in the reaction zone, the species preferably comprises rhodium complexed with (a) a ligand defined by the above structural formula in a molar ratio of ligand/Rh of about 1/1, (b) H in an atomic ratio of H/Rh of about 1/1, and (c) carbon monoxide in a molar ratio of CO/Rh of about 2/1.

The present process is carried out preferably in a gas sparged reactor such that the catalyst which is dissolved in a high boiling organic solvent under pressure does not leave the reaction zone with the aldehyde product which is taken overhead by the unreacted gases. This overhead gases are then chilled in a vapor liquid separator to condense out the aldehyde product, the gases being recycled to the reactor and the liquid product let down to atmospheric pressure for separation and purification by conventional techniques. A side draw from the reactor preferably is provided so that a small amount of the catalyst can be withdrawn at a desirable rate for more complete distillation and/or regeneration and returned to the reactor after the addition of make-up ligand thereto.

The metal catalyst components are charged preferably with solvent to the reactor through suitable pressurized pumping means, preferably in their soluble forms, e.g., their carboxylate salts or mineral acid salts or the like well known to the art as disclosed, for example, in U.S. Pat. No. 2,880,241. Charged therewith or separately is one or more of the present modifying ligands in amounts such that the molar ratio of ligand to rhodium in the reactor is from about 1.0 to about 200 or more, preferably from about 2.0 to about 10.0, and most preferably from about 2.3 to about 4.0.

In the process, the syn gas is introduced into the reactor in a continuous manner by means, for example, of a primary compressor, and the ratio of hydrogen to carbon monoxide in the feed may be selected according to the particular olefin being hydroformylated and the reaction conditions present, as is well known in the art. Generally, the molar ratio of hydrogen to carbon monoxide in the reactor is maintained within the range of about 0.5 to about 4.0, but it has been found in many hydroformylations that the rate of reaction as well as yield of the desired product may be increased by increasing the hydrogen to carbon monoxide molar ratio above 4.0, and up to about 10.0 or more. In the reactor zone the syn gas preferably is present in a molar excess (total moles of $H_2+CO$) with respect to the olefin and the molar ratio varies typically from about 0.5 to about 20, preferably from about 1.2 to about 6. In a liquid overflow reactor, the above molar ratio may have a lower limit of about 0.02.

The olefin is fed to the reactor by means of suitable pumps capable of operating under substantial pressures, and the feed rates of the olefin and syn gas are selected to maintain the above-recited molar ratios of these reactants in the reactor. Typical olefins to which the present invention is applicable include straight or branched chain $\alpha$-olefins containing from 2 to 20 carbon atoms and preferably from 2 to 10 carbon atoms, and optionally containing groups or substituents which do not interfere with the hydroformylation process. Illustrative of such $\alpha$-olefins are ethylene, propylene, 1-butene, 2-methylpropylene, 2-methyl-1-butene, 1-pentene, 1-hexene, 1-heptene, 1-octene, 2-ethyl-1-hexene, 1-dodecene, 1-octadecene, and allyl alcohol. If desired, mixtures of olefins, particularly ethylene and propylene, can be fed to the reactor.

Any suitable solvent which does not adversely affect the hydroformylation process and which is inert with respect to the catalyst, olefin feed, syn gas and the hydroformylation products may be used. Inert solvents of this nature are well known to those skilled in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents are those which are sufficiently high boiling to remain for the most part in the gas sparged reactor, and include TEXANOL® (2,2,4-trimethyl-1,3-pentanediol monoisobutyrate) solvent and its isomers, and the by-products such as alcohols, esters, acetals, and hydroxyaldehydes produced in the hydroformylation reaction and retained as high boiling liquids at the bottom of the subsequent distillation columns.

Aldehyde product also may be prepared batchwise with the present invention by contacting the olefin, hydrogen, and carbon monoxide with the present catalyst in an autoclave. High boiling aldehyde products such as normal nonanal may be prepared in a continuous manner with the aldehyde product being removed from the reactor zone as a liquid in combination with the catalyst. The aldehyde product may be separated from the catalyst by conventional means such as by distillation, and the catalyst then recycled back to the reactor. It will be apparent to those skilled in the art that other reactor schemes may be used with this invention.

The present process can be carried out with very small amounts of catalyst containing from about $1\times10^{-6}$ moles of rhodium (calculated as Rh°) per mole of olefin in the reactor zone. However, such low catalyst concentrations are not commercially desirable since the reaction rates are low. The upper catalyst concentration is essentially unlimited and appears to be dictated principally by the high cost of rhodium and the fact that no advantage is evident in the use of catalyst containing above about $1\times10^{-1}$ moles of rhodium per mole of olefin in the reactor zone. A concentration of from about $1\times10^{-5}$ moles to about $5\times10^{-2}$ moles of rhodium per mole of olefin is preferred, and from about $1\times10^{-4}$ to about $1\times10^{-2}$ is most preferred.

This invention will be illustrated further by the following examples although it will be understood that these examples do not limit the invention and are for purposes of illustration only.

LIGAND PREPARATION

NAPHOS was synthesized by a sequence of published procedures. The 2,2'-dimethyl-1,1'-binaphthyl was prepared from 1-bromo-2-methylnaphthalene by the method of Maigrot and Mazaleyrat, Synthesis, 317 (1985) (copy enclosed). Benzylic bromination of 2,2'-dimethyl-1,1'-binaphthyl with N-bromosuccinimide and catalytic N,N'-azobis(isobutyronitrile), by the procedure of Bestmann and Both Chem. Ber., 107, 2926 (1974) (copy enclosed), afforded 2,2'-bis(bromomethyl)-1,1'-binaphthyl. Using methods outlined by Tamao, et al in Tetrahedron Letters No. 16, pp 1389–1392, 1977, Pergamon Press, Gr. Brit., (copy enclosed), the dibromide was converted to NAPHOS (1,1) dioxide by reaction with methyl diphenylphosphinite and the dioxide was reduced with trichlorosilane/triethylamine to yield NAPHOS. It is noted that none of these references are concerned in any way with the use of NAPHOS for oxo or hydroformylation reactions.

EXAMPLE A

Preparation of Rhodium 2-Ethylhexanoate Solution in TEXANOL Solvent

The apparatus consists of a 5-liter three-necked flask equipped with a heating mantle, Teflon bladed mechanical stirrer, reflux condenser, and a thermometer. Sodium hydroxide (80 grams) was dissolved in 1,000 ml of water in the flask. 2-Ethylhexanoic acid (196 grams) was added to the flask and dissolved. Rhodium chloride hydrate (46.62 grams containing 20 grams of rhodium metal value) was dissolved in 900 ml of water separately and then added to the stirred sodium 2-ethylhexanoate solution in the flask. The mixture was heated to 95° C. and kept vigorously stirred for 1.5 hours. A dark green oil of crude product separated. The mixture was cooled to room temperature and 400 ml of TEXANOL solvent was added with stirring. The two phases were separated. The aqueous layer was reextracted with three 400 ml Texanol washes which were combined with the first organic extract. The combined organic phases were washed with 1,000 ml of water. The water wash was combined with the original water wash for rhodium analysis. The combined organic phases were filtered through a 0.5-inch thick bed of celite and made up to 2 liters volume with Texanol that was washed through the celite. The concentration of rhodium in the organic phase was 10,000 ppm and in the combined aqueous phase was 2 ppm.

EXAMPLE B

Typical Bench-Scale Low Pressure Hydroformylation of Propylene Using The Present Catalysts The reactor consists of a vertically held stainless steel 4 foot by 1 inch (inside diameter) tube having a stainless steel filter element welded into its side near the bottom. The bottom of the tube has a drain valve and the top has a side port through which the vaporized products and unreacted gases leave the reactor. The top end of the tube is provided with a screwed plug which can be removed for charging the catalyst and which contains a thermowell whereby the temperature of the catalyst solution (reaction medium) in the reactor is measured accurately. Hydrogen and carbon monoxide are fed to the reactor from cylinders via pressure regulators and flow controllers which use differential pressure cells and air actuated flow control valves to maintain accurate flow. A third feed of nitrogen from a cylinder goes to the reactor via a pressure regulator and rotameter with needle valve. The carbon monoxide passes through a heated commercial "deoxo" unit as marketed by Engelhard Industries, Division, Engelhard Minerals and Chemicals Corp., Newark, N.J., to remove oxygen impurities. The nitrogen admixed with hydrogen pass through a similar "deoxo" unit before entering the reactor. Propylene is fed as a liquid to a preheater section or plenum chamber, where it is combined with the other feed gases and is vaporized prior to entering the reactor via the stainless steel filter element. The propylene feed rate is measured using rate-of-level drop in a tank containing liquid propylene using an armored rotameter with a needle valve to control the liquid propylene feed rate.

In operation, the catalyst is contained as a solution in the lower portion of the reactor tube and the reactant gases are sparged up through the solution as bubbles emanating from the filter element. Product butyraldehyde is formed in the catalyst solution where it accumulates and eventually is removed as a vapor by vapor/liquid equilibration with unreacted gases. This type of reactor is known as a vapor take-off or vapor stripped reactor. The hot gases are cooled upon leaving the reactor through said side port and the butyraldehyde product, along with some unreacted propylene, collects in a cooled high pressure separator connected by suitable conduit means to said side port. The noncondensed gases are let down to atmospheric pressure via a back pressure regulator which controls the reactor pressure. Additional butyraldehyde is condensed out of the atmospheric pressure gas stream by passing it through a series of three dry ice traps. Once an hour the contents of the high pressure separator and dry ice traps are collected and combined. The weight of butyraldehyde product obtained during the hour and its n/iso ratio are calculated using standard gas/liquid chromatographic techniques in combination with the crude weight of the product collected. In practice, approximately one hour is required for this bench unit to reach steady state production rates where catalyst activity and n/iso product ratio remain substantially constant.

EXAMPLE 1

Hydroformylation of Propylene by Rhodium/NAPHOS Oxo Catalyst at 105° C. Using a 3/1 Hydrogen/Carbon Monoxide Mole Ratio and 30 Mol Percent Propylene in the Feed A catalyst solution was prepared by dissolving rhodium (II) 2-ethylhexanoate (containing 33.45 mg of rhodium; 0.325 mmole) in 180 ml of TEXANOL solvent under nitrogen. NAPHOS (0.53 gram; 0.813 mmole) was dissolved in 10 ml of toluene under nitrogen. The NAPHOS solution was added to the rhodium/Texanol solution and mixed under nitrogen until homogeneous. The catalyst solution was charged to the bench scale continuous gas-stripped reactor under an argon blanket. The reactor was pressured to 260 psig with hydrogen, carbon monoxide, and nitrogen and heated to 105° C. After reaching 105° C., propylene feed was started and the unit was operated at the feed rates listed below at standard temperature and pressure conditions, in Liters/Minute.

| Hydrogen | 4.31 Liters/Min |
| Carbon Monoxide | 1.44 Liters/Min |
| Propylene | 2.88 Liters/Min |
| Nitrogen | 0.96 Liter/Min |

The reactor was run under these conditions for a total of 5 hours with the butyraldehyde product collected, weighed, and analyzed by gas/liquid chromatography hourly. The net weight of butyraldehyde product averaged 124.6 grams per hour in the last 4 hours of operation. The mole ratio of normal butyraldehyde/isobutyraldehyde (n/iso ratio) over this period averaged 56.6/1. The oxo activity of the catalyst is equivalent to 8.2 pounds butyraldehyde per gram Rh-hour.

In the following Example 2, NAPHOS and several other ligands were used under essentially identical conditions to hydroformylate propylene. The runs are designated (a)–(o) in Table I and are given to show the vast improvement in N/Iso ratio achieved by the present invention.

EXAMPLE 2

The catalyst charge from Example 1 employing NAPHOS ligand was left in the reactor under 260 psig of hydrogen and carbon monoxide pressure overnight at room temperature. The reactor was heated to 125° C. and run at 260 psig. The reactant gases were fed to the reactor at the rates shown below for 5 hours.

| Hydrogen | 3.36 Liters/Min |
| Carbon Monoxide | 3.36 Liters/Min |
| Propylene | 1.92 Liters/Min |
| Nitrogen | 0.96 Liter/Min |

Butyraldehyde product was collected, weighed, and analyzed as in Example 1. The net weight of butyraldehyde product averaged 88.9 grams per hour in the last 4 hours of operation with a n/iso ratio of 20.4/1. The oxo activity of the catalyst is equivalent to 5.85 pounds of butyraldehyde per gram Rh-hour. This run is designated (a) in Table I. Runs (b)–(o) employing different ligands were made at essentially these same reactant feed rates and at the catalyst charges shown in the table.

EXAMPLE 3

Hydroformylation of 1-Octene by Rhodium/NAPHOS

A solution of rhodium (I) dicarbonylacetylacetonate (0.0377 gram; 0.146 mmole), NAPHOS (0.23 gram; 0.35 mmole) and octene-1 (31.3 ml, 22.4 grams; 0.2 mole) in toluene (69 ml) was prepared under nitrogen and placed in a nitrogen flushed 300-ml stainless steel autoclave. The autoclave was pressurized to 300 psig with 1/1 $H_2/CO$ and heated, with rapid stirring, to 105° C. When the pressure dropped to 250 psig, it was replenished to 300 psig with 1/1, $H_2/CO$. The reaction was maintained at 105° C. and 250-300 psig for 2 hours. A total pressure drop of 325 pounds was observed. After cooling to room temperature, the light yellow solution was removed from the autoclave and analyzed by gas chromatography. Results are shown in TABLE II in runs (a)-(j) wherein a variety of other ligands were also used under the same reaction conditions except where the ligand/Rh mole ratio is shown to be different. The very large improvement in N/Iso ratio for the product aldehydes as a result of the use of NAPHOS ligand is shown in TABLE 3, run (j).

EXAMPLE 4

Hydroformylation of Allyl Alcohol by Rhodium/NAPHOS

A solution of rhodium (I) dicarbonylacetylacetonate (0.0377 gram; 0.146 mmole), NAPHOS (0.23 gram; 0.35 mmole) and allyl alcohol (13.6 ml; 11.6 grams; 0.2 mole) in toluene (86 ml) was prepared under nitrogen and placed in a nitrogen flushed 300-ml stainless steel autoclave. The autoclave was pressurized to 125 psig with $H_2/CO$ (1/1 molar ratio) and heated, with rapid stirring, to 80° C. When the pressure dropped to 75 psig, it was replenished to 125 psig with additional (1/1) $H_2/CO$. The reaction was maintained at 80° C. and 75-125 psig for 30 minutes. A total pressure drop of 305 pounds was observed. After cooling to room temperature, the light yellow solution was removed from the autoclave and analyzed by gas chromatography. Conversion of allyl alcohol: 98.7 percent. Yields (based on allyl) alcohol): 4-hydroxybutyraldehyde—81.3 percent, 2-methyl-3-hydroxypropionaldehyde—13.0 percent, propionaldehyde—4.4 percent. Ratio of linear oxo aldehyde to branched oxo aldehyde—6.28/1.

TABLE 1

Comparison of Different Ligand/Rh Catalyst Systems at 260 psig

| Run | Ligand | Rh Charge, mg | Ligand Charge, mmol | L/Rh Mole Ratio | Reactor Temp, °C. | Catalyst Activity, lb HBu/g Rh-hr | HBu N/Iso Ratio |
|---|---|---|---|---|---|---|---|
| (a) | NAPHOS | 33.45 | 0.813 | 2.5/1 | 125 | 5.85 | 20.4/1 |
| (b) | TR-DMCB | 31.25 | 0.729 | 2.4/1 | 125 | 5.05 | 4.36/1 |
| (c) | TR-DMECB | 31.25 | 0.729 | 2.4/1 | 125 | 4.41 | 4.23/1 |
| (d) | TR-DPNOR | 31.25 | 0.729 | 2.4/1 | 125 | 4.07 | 4.32/1 |
| (e) | CIS-DPNOR | 31.25 | 0.729 | 2.4/1 | 125 | 2.44 | 2.67/1 |
| (f) | 1,8-DINAP | 31.25 | 0.729 | 2.4/1 | 125 | 0.84 | 0.95/1 |
| (g) | FL | 31.25 | 0.729 | 2.4/1 | 125 | 5.00 | 3.56/1 |
| (h) | CIS-1,2DPCH | 31.25 | 0.729 | 2.4/1 | 125 | 1.39 | 2.03/1 |
| (i) | DIOP | 31.25 | 0.729 | 2.4/1 | 125 | 5.16 | 4.02/1 |
| (j) | 1,4-BUT | 31.25 | 0.729 | 2.4/1 | 125 | 1.25 | 2.45/1 |
| (k) | 1,3-PROP | 31.25 | 0.729 | 2.4/1 | 125 | 0.97 | 0.84/1 |
| (l) | 1,5-PENT | 31.25 | 0.729 | 2.4/1 | 125 | 2.32 | 2.28/1 |
| (m) | 1,6-HEX | 31.25 | 0.729 | 2.4/1 | 125 | 4.00 | 1.51/1 |
| (n) | O-XYL | 31.25 | 0.729 | 2.4/1 | 125 | 3.10 | 2.41/1 |
| (o) | TPP | 15.00 | 18.13 | 124/1 | 125 | 9.41 | 2.43/1 |

Above Ligand Identifications
TR-DMCB = trans-1,2-bis(diphenylphosphinomethyl)-3,3-dimethylcyclobutane
TR-DMECB = trans-trans-1,2-bis(diphenylphosphinomethyl)-3-ethoxy-4,4-dimethylcyclobutane
TR-DPNOR = trans-2,3-bis(diphenylphosphinomethyl)[2.2.1]bicycloheptane
1,8-DINAP = 1,8-bis(diphenylphosphinomethyl)naphthalene
CIS-DPNOR = endo, cis-2,3-bis(diphenylphosphinomethyl)[2.2.1]bicycloheptane
FL = 1,1'-bis(diphenylphosphino)ferrocene
CIS-1,2DPCH = cis-1,2-bis(diphenylphosphinomethyl)cyclohexane
DIOP = (-)-2,3-O-isopropylidene-2,3-dihydroxy-1,4-bis(diphenylphosphino)butane
1,4-BUT = 1,4-bis(diphenylphosphino)butane
1,3-PROP = 1,3-bis(diphenylphosphino)propane
1,5-PENT = 1,5-bis(diphenylphosphino)pentane
1,6-HEX = 1,6-bis(diphenylphosphino)hexane
O-XYL = a,a'-bis(diphenylphosphino)orthoxylene
TPP = triphenylphosphine

TABLE 2

Batch Autoclave Hydroformylations of Octene-1

| Run | Ligand | L/Rh Ratio | % Conversion Octene-1 | % Yield to Isooctene[b] | % Yield to $C^9$ Aldehyde of Olefin Fed |
|---|---|---|---|---|---|
| (a) | O-XYL | 2.4/1 | 94.3 | 3.7 | 90.6 |
| (b) | TR-DMCB | 2.4/1 | 97.1 | 2.8 | 94.3 |
| (c) | FL | 2.4/1 | 93.6 | 3.1 | 90.5 |
| (d) | TPP | 150/1 | 98.4 | 3.5 | 94.9 |
| (e) | DIOP | 2.4/1 | 98.1 | 4.3 | 93.8 |
| (f) | BDPP[a] | 5/1 | 99.2 | 2.9 | 96.3 |
| (g) | 1,4-BUT | 2.4/1 | 95.3 | 2.7 | 92.6 |
| (h) | 1,5-PENT | 2.4/1 | 98.4 | 2.6 | 95.8 |
| (i) | 1,3-PROP | 2.4/1 | 67.0 | 1.9 | 65.1 |

TABLE 2-continued

Batch Autoclave Hydroformylations of Octene-1

| Run | Ligand | L/Rh Ratio | % Conversion Octene-1 | % Yield to Isooctene[b] | % Yield to C9 Aldehyde of Olefin Fed |
|---|---|---|---|---|---|
| (j) | NAPHOS | 2.4/1 | 98.1 | 7.2 | 90.9 |

[a]BDPP - n-Butyldiphenylphosphine.
[b]Mixture of octene-2 and octene-3 isomers.

TABLE 3

| | % Isomer Distribution of C9 Aldehyde | | | | |
|---|---|---|---|---|---|
| Run | n-Nonanal | 2-Methyl octanal | 2-Ethyl heptanal | 2-Propyl hexanal | N/Branched Aldehyde Ratio |
| (a) | 77.64 | 22.32 | 0.05 | 0.00 | 3.47/1 |
| (b) | 87.2 | 12.74 | 0.06 | 0.00 | 6.81/1 |
| (c) | 82.8 | 17.19 | 0.05 | 0.00 | 4.80/1 |
| (d) | 77.2 | 21.49 | 0.77 | 0.04 | 3.46/1 |
| (e) | 85.12 | 14.70 | 0.189 | 0.00 | 5.72/1 |
| (f) | 72.82 | 25.02 | 1.99 | 0.164 | 2.68/1 |
| (g) | 75.16 | 24.75 | 0.081 | 0.00 | 3.03/1 |
| (h) | 73.35 | 26.14 | 0.507 | 0.00 | 2.75/1 |
| (i) | 49.10 | 50.78 | 0.115 | 0.00 | 0.96/1 |
| (j) | 97.11 | 2.73 | 0.16 | 0.00 | 33.60/1 |

The invention has been described in detail with particular reference to preferred embodiments thereof, but it will be understood that variations and modifications can be effected within the spirit and scope of the invention.

We claim:

1. A hydroformylation process comprising contacting at least one olefin having from 2 to 20 carbon atoms in a reaction zone at a temperature of from about 20° C. to about 250° C. and a pressure of from about 15 psig to about 800 psig with hydrogen, carbon monoxide, and a catalyst comprising rhodium in chemical complex with one or more ligands of the general formula

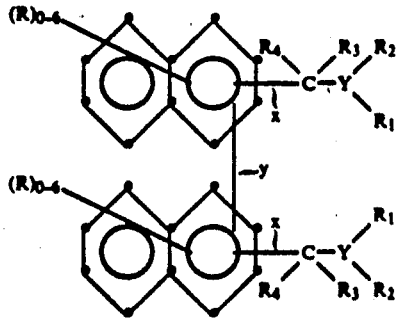

wherein:
the x bonds are adjacent the y bonds on the ring structures;
each R when present as a substituent is independently selected from alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;
each $R_1$ and $R_2$ is independently selected from alkyl, aryl, aralkyl, alkaryl or cycloaliphatic;
each $R_3$ and $R_4$ is independently selected from hydrogen and the $R_1$ substituents;
wherein each of the above alkyl groups or moieties is straight or branched chain of 1–20 carbons, each aryl group contains 6–10 ring carbons, and each cycloaliphatic group contains from 4–6 ring carbons; and
each Y is independently selected from the elements N, P, As, Sb and Bi;
for a sufficient period of time to permit reaction of said hydroformylation stock with said carbon monoxide and hydrogen to form aldehyde product.

2. The process of claim 1 wherein each said alkyl group or moiety is from 1–8 carbons.

3. The hydroformylation process according to claim 1 wherein said reaction zone is operated at temperatures between about 80° C. and 150° C. and at pressures between about 100 psig and 400 psig, and the molar ratio of ligand to rhodium is from about 1.0 to about 200.

4. The hydroformylation process according to claim 3 wherein the molar ratio of said hydrogen to carbon monoxide is at least 0.5, and the total moles of hydrogen and carbon monoxide are present in said reaction zone in the ratio range of from about 0.02 to about 20 with respect to moles of said olefin.

5. The hydroformylation process according to claim 4 wherein said olefin is selected from one or more of ethylene, propylene, 2-methylpropylene, 2-butene, 1-butene, 2-methyl-1-butene, 1-pentene, 1-hexene, 1-heptene, 1-octene, allyl alcohol, allyl acetate, methyl vinyl ether, ethyl vinyl ether, allyl ethyl ether, vinyl acetate and acrolein diethyl acetal.

6. The hydroformylation process according to claim 1 wherein said rhodium is present in said reaction zone in an amount between about $1 \times 10^{-6}$ to about $1 \times 10^{-1}$ moles per mole of said olefin present in said reaction zone.

7. The process of any one of claims 1–6 wherein said ligand has the formula

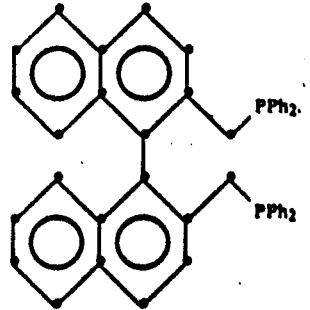

8. The process of claim 7 wherein the olefin is propylene.

9. The process of claim 7 wherein the molar ratio of ligand to rhodium is from about 1 to about 10.

10. The process of claim 7 wherein the molar ratio of ligand to rhodium is from about 2.3 to about 4.

* * * * *